United States Patent [19]

Maronian

[11] Patent Number: 5,069,227

[45] Date of Patent: Dec. 3, 1991

[54] PROPHYLACTIC DEVICE HAVING PATHOGEN RESISTANT BARRIER

[75] Inventor: Hovaness Maronian, Rochester, N.Y.

[73] Assignee: Rochester Medical Devices, Inc., Rochester, N.Y.

[21] Appl. No.: 617,391

[22] Filed: Nov. 20, 1990

Related U.S. Application Data

[63] Continuation of Ser. No. 261,050, Oct. 21, 1988, abandoned.

[51] Int. Cl.$^5$ .............................................. A61F 6/04
[52] U.S. Cl. .......................................... 128/844; 427/2
[58] Field of Search .................... 427/2, 171; 128/844; 604/347-352

[56] References Cited

U.S. PATENT DOCUMENTS

| | | | |
|---|---|---|---|
| 4,388,164 | 6/1983 | Moll et al. | 427/171 X |
| 4,817,593 | 4/1989 | Taller et al. | 128/844 |
| 4,935,260 | 6/1990 | Shlenker | |

FOREIGN PATENT DOCUMENTS

| | | |
|---|---|---|
| 1566376 | 4/1970 | Fed. Rep. of Germany . |
| 1616474 | 4/1971 | Fed. Rep. of Germany . |
| 8800818 | 2/1988 | PCT Int'l Appl. . |
| 927369 | 5/1963 | United Kingdom . |
| 1154571 | 6/1969 | United Kingdom . |
| 2065718 | 7/1981 | United Kingdom . |

OTHER PUBLICATIONS

Translation of German OLS Publication No. 1616474 to Asaka et al., PTO 90-3150, U.S. Patent and Trademark Office, Washington, D.C., Jun. 1990.
Maronian, Application Ser. No. 07/423899, filed Oct. 19, 1989.

Primary Examiner—Evan Lawrence
Attorney, Agent, or Firm—Birch, Stewart, Kolasch & Birch

[57] ABSTRACT

An elastic prophylactic device having an improved ductile metal barrier layer to prevent the transmission of virus, such as those causing AIDS or HERPES. The improved metal barrier is formed in such manner as to enable it to repeatedly expand and contract in concert with the elastic movements of the prophylactic device during its intended use, without fracture or breaking of the barrier metal layer. A number of processes for manufacturing the improved device are given, including initially stretching the elastic membrane of the device to the extent of its intended use, and vapor depositing a ductile metal in a thin, continuous coating onto the stretched membrane.

20 Claims, No Drawings

PROPHYLACTIC DEVICE HAVING PATHOGEN RESISTANT BARRIER

This application is a continuation of application Ser. No. 07/261,050 filed on Oct. 21, 1988, now abandoned.

STATEMENT OF INVENTION

This invention generally relates to improvements in prophylactic devices widely used for birth control and prevention of disease, and more particularly to such devices having improved resistance to the transmission of very small virus, such as those causing AIDS and HERPES. This invention also relates to methods of making such improved devices.

BACKGROUND

Prophylactic devices for the prevention of sexual disease, as used in large numbers throughout the world, are most often made of natural rubber latex material in very thin wall thicknesses ranging from 0.03 millimeters 30 micromillimeters) to 0.07 millimeters ( 70 micromillimeters). Such very thin membranes of highly elastic natural materials have been found most desirable to minimize interference with active movement during use as well as permitting the users to retain the nerve sensations and experiences during such use.

However, natural rubber material, in such thin wall membranes, does not provide a continuous, impermeable barrier to the passage of micro-size pathogens, such as the virus causing AIDS or HERPES. Such virus are known to be as small as 0.1 micromillimeter (0.001 millimeter), or about 250 times smaller than the length of the human sperm and at least 30 times smaller than the thickness of such sperm. The natural rubber membrane is comprised of a polymer matrix characterized by myriads of randomly distributed microsize openings or pores formed among the polymer chains. Thus although such natural rubber prophylactics have been found to be an effective barrier preventing the transmission of the larger sperm, there is no assurance that such devices are effective in preventing the transmission of such much smaller virus, and some testing to date has indicated to the contrary.

Additionally, the elastic membrane is cyclically stretched and relaxed in three dimensions during its intended use, resulting in repeated stressing of the membrane and reductions in its wall thickness, during such use. This action is believed to result in repeatedly enlarging and reducing the micro-size openings in the membrane, thereby increasing the probability of pathogens passing through the membrane.

Still further, despite extensive quality control testing of the prophylactics during manufacture, the membranes are not manufactured with absolutely uniform wall thicknesses, whereby during use different areas of the walls are not uniformly stressed nor uniformly stretched, resulting in "weaker spots" or areas and occasional bursting under severe stressing. The International Planned Parenthood Federation estimates that even from the best manufacturers, the prophylactics have a bursting rate during use of 0.1% whereas those from the worst manufactured brands have a burst rate as high as 1%.Similar statistical data is not yet available, or has been published, with respect to the effectiveness of rubber prophylactics in preventing the transmissiion of virus, such as those causing AIDS and HERPES. It is widely believed, however, that presently available prophylactics are not very effective in preventing the transmission of such sexually transmitted diseases.

SUMMARY OF THE INVENTION

According to the present invention it has been found that a substantially continuous thin, ductile metal coating or layer may be provided over the surface of the prophylactic device, without fracture or breaking despite repeated stretching and relaxing of the device such as would occur during intended use. This is accomplished by forming the metal layer in such fashion that it can be repeatedly expanded and contracted, with the elastic membrane, without fracturing or breaking of the thin metal layer. According to one preferred manufacturing process, the elastic membrane is initially stretched to the extent of its intended use, and a continuous coating of highly ductile metal is thinly applied to the stretched membrane to seal its surface. In another process, the stretched membrane is initially thinly coated with an additional elastic material, and the resulting coated device permitted to again relax, forming a pattern of wrinkles on its surface. The thin ductile metal seal is thereafter applied to the wrinkled surface, thereby to form a correspondingly wrinkled metal layer that can be expanded and contracted without fracture or breaking. In still a third process, the surface of the membrane is embossed or patterned, in a similar configuration of undulations or wrinkles, and is then continuously coated with a thin layer of highly ductile metal, thereby to provide an expandable metal seal.

DETAILED DESCRIPTION OF PREFERRED EMBODIMENTS

According to the present invention it has been found that micro-size openings that are formed in conventionally manufactured prophylactic articles, of natural latex rubber and other elastic materials, can be sealed by a continuous, thin film, coating, or layer of a ductile metal, such as aluminum; and that such a seal can be maintained despite repeated stretching and relaxing of the elastic article without fracturing or cracking the thin metal layer. This is performed by using a highly ductile metal for the layer and by forming the layer with undulations, folds, or wrinkles in its thickness, such that the metal layer can be expanded and contracted to progressively smoothen the folds and restore the folds, without fracture or breaking of the metal seal.

In one preferred process of manufacture, a conventional prophylactic article of natural latex rubber is prestretched on a mold to the extent expected during use, and is coated with substantially pure aluminum, in a vacuum deposition chamber, to form a thin, continuous film of aluminum directly onto the surface of the rubber article. The coating process is continued to form a metal film having a thickness ranging from 500 Angstroms to 1500 Angstroms.

To insure that the deposited metal layer properly adheres to the stretched elastic article, the surface of the rubber is carefully cleaned by chemical solvents, and/or by other cleaning methods either mechanical or electrical, prior to metalizing the surface.

Upon completion of the coating process, the metalized article is removed from the vacuum chamber, and from its expansion mold, and permitted to relax to the normal relaxed size of the article.

EXAMPLE 1

A prophylactic article of standard commercial manufacture was stretched in a mold in two dimensions to twice its normal length and thickness ( 100%). Its outside surface was then cleaned of contaminants by being awabbed with isopropyl alcohol. The mold was then placed in a CYC thermal evaporator of conventional commercial design, and vacuum metallized at a vacuum of about 10 TORR. The ductile metal used for coating was 99.7% pure aluminum, and this metal was resistance fired in the evaporator for a period of about (7) seven seconds. To obtain a more uniform coating on the article, the mold was supported on a revolving rack "cluster" inside of the evaporator, and revolved about five (5) times during a seven (7) second coating interval.

After metallized coating, the article was removed from the evaporator, and from its expansion mold, and permitted to resume its relaxed elastic state. It was then subjected to various tests, including an electrical conductivety test, and various observation tests under a 50 power microscope. These tests initially confirmed the continuity of the metal film over the article. The coated article was then subjected to repeated cycles of stretching and relaxation, within the 100% limit of its coating, while under microscopic examination. These tests revealed the undulated, wrinkled, or folded, surface configuration of the metal layer when the article was disposed in a relaxed state, and the progressive smoothing of the metal undulations, wrinkles, and folds as the elastic article was stretched. No fracturing, cracking, or breaking of the aluminum film was observed under the microscope during the repeated cyclical stretching and relaxing of the elastic article. The electrical conductivety tests also did not reveal any breaks in the electrical conductivety of the aluminum film during the repeated stretching and relaxing of the article.

EXAMPLE 2

A prophylactic article of standard commercial manufacture was stretched on a mold in three dimensions to one half greater (50%) than its normal length and diameter, and aluminum metallized in a vacuum evaporator in the same manner as in EXAMPLE 1, above.

The same tests. as in EXAMPLE 1, were conducted, but the cyclically repeated stretching and relaxing of the metalized article were limited to an extent only 50% greater than the relaxed length and diameter of the article. The test results were the same as found in EXAMPLE 1.

EXAMPLE 3

The same process as in EXAMPLES 1 and 2 was conducted but the prophylactic was prestretched only 10% greater in size than in its relaxed state.

The resulting article was tested in the same manner as in EXAMPLES 1 and 2, but was stretched during testing by only up to 10% greater than in its relaxed state.

The test results were the same as found in EXAMPLES 1 and 2.

EXAMPLE 4

The same metallizing process, of EXAMPLES 1,2,and 3 above, was performed using a standard, comercially available prophylactic article, but the elastic article was not prestretched during the metallizing of its surface with aluminum. Instead the article was placed on a non-expansion mold and accordingly metal coated while in its relaxed state.

The resulting product was tested in the same manner as in EXAMPLES 1,2,and 3 above; including cyclically stretching and relaxing the article while microscopically observing the metal surface, and electrically testing the metal surface.

The stretching of this article produced fractures, cracks, and crazing in the metal film layer that were observable under the microscope.

EXAMPLE 5

The metallized article samples in EXAMPLES 1, 2, and 3 were each subjected to additional cycles of repeated stretching and relaxing but were expanded during stretching to a degree beyond the limit of their prestretching during the metallizing processes.

In all examples, when the articles were expanded beyond their prestretched limits during coating, the tests revealed fracturing, cracking, and crazing of the aluminum film.

More specifically:

For the samples of EXAMPLE 1: Cracks were found when expanded beyond 100% of the articles relaxed size.

For the samples of EXAMPLE 2: Cracks were found when expanded beyond 50%.

For the samples of EXAMPLE 3: Cracks were found when expanded beyond 10%.

For the samples of EXAMPLE 4: Cracks were found for any expansion.

ADDITIONAL EXAMPLES

A series of additional prophylactic articles of standard commercial manufacture were metallized with aluminum using the same process as described above, in EXAMPLES 1,2,and 3. However, the aluminum layers were coated to twice the thickness as in these examples eg 1000 Angstroms to 1500 Angstroms).

Each of these metalized articles were tested in the same manner as the corresponding one in the above EXAMPLES. The test results were found to be the same for the thicker aluminum films or layers than for the thinner aluminum layers.

In addition to aluminum, a number of other ductile metals may be used to provide the very thin metal seal over the article, including gold, silver, platinum, and other metals, including metal alloys. All of these very ductile metals can be applied in very thin coatings to the elastomeric surface of the article by a vacuum vaporization process, as described, or by other known processes for coating metals, including metal sputtering and electroless plating. Such otherplating methods may be more useful where the article is made fromother substrate materials, other than natural latex rubber, where such other materials cannot be plated by metal vaporization.

Alternatively, the metal film seal may be provided by plating a series of ductile metal films to the surface, instead of a single coating. Each of the different layers may be of the same metal, or of different ductile metals, and with each layer being applied successively over the previous layer.

According to the present invention it has been found that a minimum thickness of the metal must be coated to insure obtaining a continuous metal sealing of the surface of the article. This minimum thickness of the metal film depends upon a number of parameters, including the ductile metal being used, the process of forming the metal film, and the substrate material used in the prophylactic article. Although natural rubber latex is the most widely used material for such articles, a number of other materials are in lesser use, including polyurethane and others. It has also been found that the plated thickness of this metal film can exceed the minimum thickness by about one order of magnitude, as shown by the ADDITIONAL EXAMPLES, discussed above, without impairing the performance of the metal seal or barrier, despite repeated stretching and relaxing of the article.

For the purpose of protecting the thin metal layer against abrasion, thin film of suitable lubricant, such as silicone oil, may be later applied over the metal coating. Alternatively, the metal film can be overcoated with a very thin layer of the same elastomeric material, as is used in the article, or other suitable elastomeric material can be used. This thin protective overlayer is applied over the metal film while the article is still on its stretching mold. In this manner, the elastomeric overlayer conforms to the undulations, wrinkles, and folds in the metal film that are formed when the article is removed from the mold and elastically contracted to its relaxed state.

OTHER PROCESSES

A number of alternative processes for making the improved article may be used.

In an alternative process, the prophylactic article may be prestretched, as before, to an extent expected during use, and the expanded article can be precoated with a thin intermediate layer of the same elastomeric material, such as natural latex rubber. This precoating of the stretched article with an elastomer may be performed in the same manner, by dip-coating, as is usually used in the manufacture of such articles.

After precoating, the article is removed from its stretching mold and permitted to elastically contract to its relaxed state. The shrinking of the article correspondingly shrinks the intermediate elastomeric layer, producing undulations, wrinkles, and folds in the surface of the intermediate layer as the article is relaxed. The wrinkled intermediate layer is then metalized or coated with a thin layer of aluminum, or other ductile metal, to provide a continuous metal covering and seal, covering the undulations, wrinkles, and folds in the intermediate layer.

In the same manner as discussed above, the resulting metallized article can be repeatedly stretched and relaxed, within the limit of the original stretching, without fracture, cracking, or breaking of the metal sealing film. Stretching of the article tends to progressively smooth the undulations, folds, and wrinkles in both the intermediate layer and in the correspondingly undulated metal layer, without destroying the integrity of the metal seal or barrier.

According to a still further process of making the improved article, the outer surface of the elastomeric article is patterned to provide indulations in its outer surface, including a pattern of wrinkles or folds, thereby to increase its surface area. This can be performed by mechanical abrasion, or by chemical etching, or by optical or electrical cutting means, including a laser beam or an electron beam, respectively. This patterning of its surface is performed while the article is disposed on a mold and maintained in its relaxed state. A thin coating or film of ductile metal, such as aluminum, is then applied over the undulated surface, following and sealing the undulations, folds, and wrinkles in a continuous covering. The metal film is applied by vapor deposition under a vacuum, as previously described, or by metal sputtering, or electroless deposition. In the same manner as previously described, the resulting metallized article can be repeatedly stretched and relaxed without fracture, cracking, or breaking of the thin ductile metal layer. Instead, stretching of the article, within the limits imposed by the patterned surface, results in ductilely expanding the outer metal layer, smoothing the undulation, wrinkles, and folds in the metal film.

It will be appreciated by those skilled in the art, that the size and number of the indulations, wrinkles, and folds formed in the ductile layer determines the extent that the metal film can be expanded while maintaining its structural integrety. The elastomer prophylactic member is also initally made thicker than usual to provide the necessary strength without tearing when the article is repeatedly stretched.

In the processes described above, the elastomeric article is disclosed or assumed, to be preformed in its conventional tubular shape, and manufactured by conventional processes, such as dip-coating of the mold in liquid rubber latex material. The metallizing is performed by vacuum deposition, or other coating process while this tubular article is supported on a mold. However, it is known to manufacture prophylactic articles from a flat elastomer sheet, by vacuum forming or blow molding the rubber sheet, as described in U.S. Pat. No. 4,576,156. According to the present invention, the same metallizing processes described above, may be applied to the elastomer in sheet form, prior to the vacuum forming or blow molding of the sheet into the tubularly shaped article.

Many other changes or variations of the article or processes may be made by those skilled in the art, without departing from the spirit and scope of the present invention. Accordingly, this invention is to be considered as being limited only by the following claims.

What is claimed is:

1. A prophylactic device having an improved barrier to resist the transmission of sexually transmitted virus, including those causing AIDS and HERPES comprising:

a hollow article having a continuous thin elastic membrane wall that is preshaped to anatomically conform to portions of the body and provide a physical barrier resisting the transmission of pathogens, said thin elastic membrane wall being capable of cyclical elastic stretching and relaxing without normally experiencing a permanent set or fracturing or tearing of the membrane wall, said membrane wall being characterized as comprising a matrix having submicroscopically small pores formed therein during manufacture, with said pores tending to enlarge during stretching of the membrane and to contract during relaxation of the membrane from its stretched condition, a thin layer of ductile metal on an outer surface of the membrane wall for sealing the pores therein, said ductile metal layer having an undulating surface when the membrane wall is in a relaxed state, said metal layer's undulating surface being extended and progressively smoothed as the membrane is elastically expanded, without breaking or fracturing of the metal layer, said metal layer improving the barrier resistance of the prophylactic member to the passage of pathogens therethrough, despite cyclically repeated elastic stretching and relaxing of the membrane.

2. A prophylactic device as recited in claim 1, wherein said thin ductile metal layer is vacuum deposited directly onto the outer surface of the elastic membrane wall.

3. A prophylactic device as recited in claim 1, wherein said ductile metal layer comprises aluminum.

4. A prophylactic device as recited in claim 1, wherein said membrane wall comprises natural latex rubber or polyurethane.

5. A prophylactic device as recited in claim 1, wherein said membrane wall comprises polyuretahne.

6. A prophylactic device as recited in claim 1, wherein said ductile metal layer is vacuum deposited as a vapor onto the outer surface of said elastic membrane wall, while the membrane wall is elastically stretched.

7. A prophylactic device as recited in claim 1, wherein the ductile metal layer has a thickness of from 5---1500 Angstroms.

8. A prophylactic device as recited in claim 1, wherein said ductile metal layer comprises aluminum.

9. A prophylactic device as recited in claim 1, wherein the elastic membrane wall comprises polyurethane.

10. A prophylactic device as recited in claim 6, wherein the elastic membrane wall comprises natural latex rubber.

11. A prophylactic device having improved barrier resistance to the passage of pathogens, including the virus causing AIDS comprising:
a thin elastic membrane that is normally capable of cyclically repeated stretching and relaxing while retaining its structural integrity,
said membrane having plural microsizes openings formed therein during manufacture that are subject to enlargement when the membrane is elastically stretched,
a thin ductile metal coating continuously covering an outer surface of the membrane for sealing the membrane and preventing the passage of pathogens through the microsized openings in the membrane,
said metal coating having an undulating surface which resembles microfolds and wrinkles when the membrane is in a relaxed state, with the wrinkles appearing to progressively spread apart and smooth out as the membrane is progressively stretched, thereby retaining the structural integrity of the metal coating without breaking or fracturing as the membrane is elastically stretched,
the metal coating providing an improved barrier to the passage of pathogens despite cyclically repeated stretching and relaxing of the membrane.

12. A prophylactic device as recited in claim 11, wherein said elastic membrane comprises natural latex rubber.

13. A prophylactic device as recited in claim 11, wherein said elastic membrane comprises polyuretahne.

14. A prophylactic device as recited in claim 11, wherein said ductile metal coating is vacuum deposited directly onto the outer surface of the elastic membrane.

15. A prophylactic device as recited in claim 11, wherein said ductile metal coating comprises aluminum.

16. A prophylactic device as recited in claim 11, wherein said ductile metal coating is vacuum deposited as a vapor onto the outer surface of said elastic membrane while the elastic membrane is elastically stretched.

17. A prophylactic device as recited in claim 16, wherein the ductile metal layer has a thickness of from 500-1500 Angstroms.

18. A prophylactic device as recited in claim 16, wherein said ductile metal layer comprises aluminum.

19. A prophylactic device as recited in claim 16, wherein the elastic membrane comprises polyurethane.

20. A prophylactic device as recited in claim 16, wherein the elastic membrane comprises natural latex rubber.

* * * * *